(12) United States Patent
Lintula

(10) Patent No.: US 11,357,901 B2
(45) Date of Patent: Jun. 14, 2022

(54) SURGICAL SUCTION FILTER

(71) Applicant: Sustain Medical, LLC, Fishers, IN (US)

(72) Inventor: Eric Lintula, Wilmington, NC (US)

(73) Assignee: SUSTAIN MEDICAL, LLC, Fishers, IN (US)

( * ) Notice: Subject to any disclaimer, the term of this patent is extended or adjusted under 35 U.S.C. 154(b) by 923 days.

(21) Appl. No.: 16/152,594

(22) Filed: Oct. 5, 2018

(65) Prior Publication Data

US 2020/0108185 A1    Apr. 9, 2020

(51) Int. Cl.
*A61M 1/00* (2006.01)
*B01D 46/24* (2006.01)
*B01D 46/00* (2022.01)

(52) U.S. Cl.
CPC ........... *A61M 1/79* (2021.05); *B01D 46/0004* (2013.01); *B01D 46/0005* (2013.01); *B01D 46/2403* (2013.01); *B01D 2265/029* (2013.01); *B01D 2275/201* (2013.01); *B01D 2275/30* (2013.01); *B01D 2279/00* (2013.01)

(58) Field of Classification Search
CPC . A61M 1/79; B01D 46/0004; B01D 46/0005; B01D 46/2403
USPC ......................................................... 604/46
See application file for complete search history.

(56) References Cited

U.S. PATENT DOCUMENTS

| | | | |
|---|---|---|---|
| 2,061,119 A * | 11/1936 | Voigt | A47J 31/0631 210/474 |
| 3,889,657 A * | 6/1975 | Baumgarten | A61M 1/79 606/119 |
| 4,957,492 A | 9/1990 | McVay | |
| 6,666,638 B2 | 12/2003 | Craven | |
| 8,075,604 B2 | 12/2011 | Denis et al. | |
| 8,484,986 B2 | 7/2013 | Lampropoulos et al. | |
| 2004/0055470 A1* | 3/2004 | Strauser | B01D 50/20 96/417 |
| 2011/0082338 A1 | 4/2011 | Fischvogt et al. | |

* cited by examiner

*Primary Examiner* — Phillip A Gray
(74) *Attorney, Agent, or Firm* — Maginot Moore Beck LLP

(57) ABSTRACT

A filter assembly for use with a surgical suction tool for removing fluid and debris from a surgical site includes a conical filter element with a plurality of orifice arrays spaced along the length of the conical body with successively decreasing orifice diameters. The filter element includes an annular flange at the mouth of the filter element that is clamped between a container and a cap. The container includes conically tapered wall to define a radial space between the container and the filter element to permit fluid flow around the filter element and through the container to an outlet tube fitting. A cap covers the mouth of the container with a threaded interface defined between the cap and the container. The threaded interface includes a dual pitch triple lead thread with a coarse lead-in pitch and a fine trailing pitch.

9 Claims, 5 Drawing Sheets

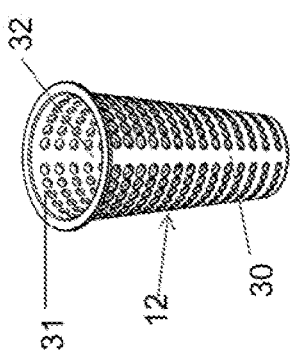
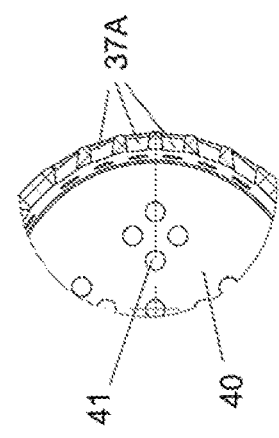
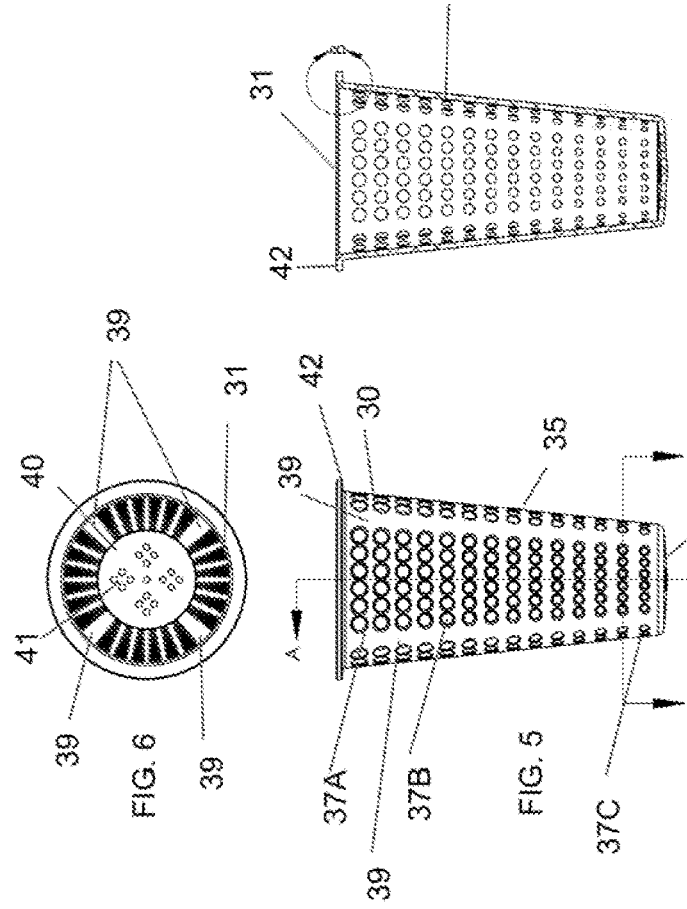
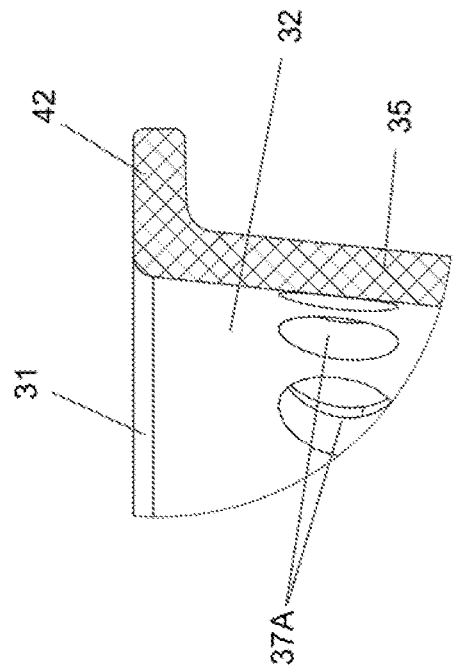

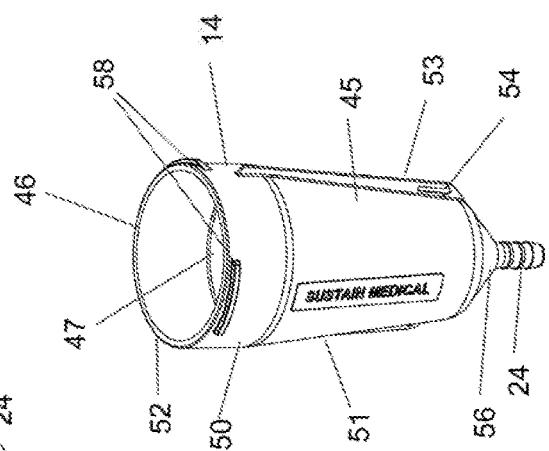
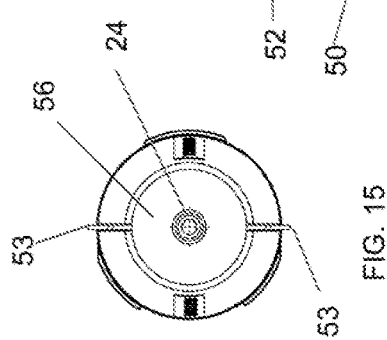
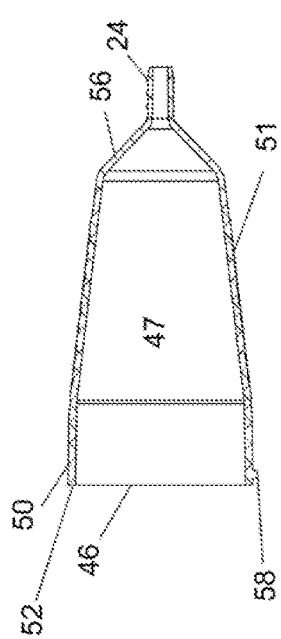
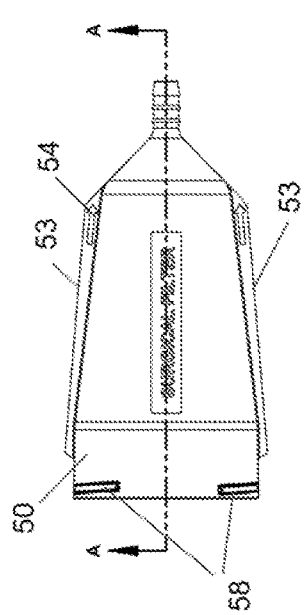
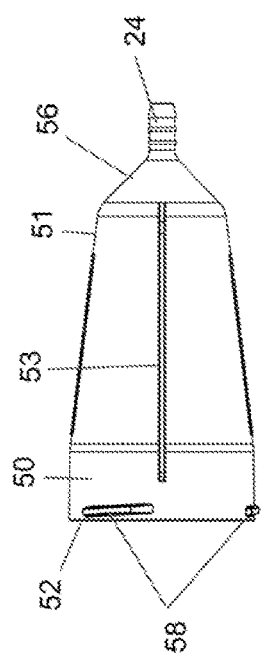
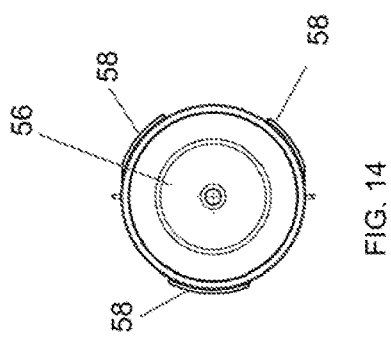

SURGICAL SUCTION FILTER

BACKGROUND

The present disclosure relates to surgical filters, and particularly to filters for use in suctioning blood, biological materials and waste matter from a surgical site.

In orthopaedic surgical procedures it is common to apply suction to the surgical site to remove blood, irrigation fluid and debris as needed for visibility of the anatomy at the site. In many cases, the debris can include bone material, surgical cement and soft tissues that can clog the suction apparatus and the path to the waste receptacle. Consequently, it is common to incorporate a filter in the flow path from the suction tool to the waste receptacle. More specifically, the filter is integrated into the flexible tubing running from the suction tool or wand to the waste receptacle.

One problem with in-line filters of this type is that they are prone to blockage from surgical debris, such as large bone pieces. In particular, the small openings or pores of the filter element can be blocked by the debris so that the suction pressure to the suction tool is, at a minimum, reduced, and in a worst-case completely blocked. In that event, the filter element must be manually unblocked during the surgery, which inherently has a detrimental effect on the surgical procedure. Moreover, when the filter element is returned to its operative configuration the integrity of the suction path can be compromised, requiring further attention to the filter element.

There is a need for an improved in-line surgical filter that overcomes the problems of prior art filter elements.

SUMMARY OF THE DISCLOSURE

In one aspect of the disclosure, a filter assembly is provided for use with a surgical suction tool for removing fluid and debris from a surgical site. The filter assembly comprises a filter element having an elongated truncated conical body including a mouth at one end, a closed bottom at an opposite end and a conically tapered wall between the mouth and bottom to define an interior chamber. The tapered wall defines a plurality of orifice arrays spaced along the length of the conical body, each of the plurality of orifice arrays including a plurality of orifices through the wall. The plurality of orifices in each orifice array has a successively decreasing diameter with each successive orifice array along the length of the body. In one feature, the filter element further includes an annular flange at the mouth of the filter element.

A container is provided for receiving the filter element, the container including a cylindrical upper wall defining a mouth, a conically tapered wall integral with the cylindrical upper wall and a conical bottom wall integral with the conically tapered wall and terminating in an outlet tube fitting adapted to engage a surgical tube connected to a suction source and/or a fluid container. The conically tapered wall is configured to coincide with a lower portion of the conically tapered wall of the filter element when the flange of the filter element is seated on the cylindrical upper wall at the mouth of said container. The conically tapered walls of the filter element and the container define a radial space therebetween along the entire length of the filter element to permit fluid flow around the filter element and through the container to the outlet tube fitting.

The filter assembly further includes a cap sized and configured to cover the mouth of the container. The cap includes a cylindrical wall sized to encircle an upper portion of the cylindrical upper wall of the container to close the mouth and a top wall defining an inlet tube fitting adapted to engage a surgical tube connected to a suction tool. In one feature, a threaded interface is defined between the cylindrical wall of the cap and the upper cylindrical wall of the container, in which the threaded interface includes a dual pitch multiple lead thread. In specific embodiments, the threaded interface is a triple lead thread and the dual pitch attribute includes a coarse lead-in pitch and a fine trailing pitch.

BRIEF DESCRIPTION OF THE DRAWINGS

FIG. 4 is a perspective view of a filter element of the assembly shown in FIG. 1.

FIG. 5 is a side view of the filter element shown in FIG. 4.

FIG. 6 is a top view of the filter element shown in FIG. 4

FIG. 7 is a bottom view of the filter element shown in FIG. 4

FIG. 8 is an enlarged cross-sectional view of the bottom of the filter element shown in FIG. 7.

FIG. 9 is a side cross-sectional view of the filter element shown in FIG. 5.

FIG. 10 is an enlarged cross-sectional view of the top of the filter element shown in FIG. 9.

FIG. 11 is a perspective view of the container of the filter assembly shown in FIG. 1.

FIG. 12 is a side view of the container shown in FIG. 11.

FIG. 13 is a side view of the container rotated 90° from the view in FIG. 11.

FIG. 14 is a top cross-sectional view of the container shown in FIG. 13.

FIG. 15 is a bottom view of the container shown in FIG. 13.

FIG. 16 is a side cross-sectional view of the container shown in FIG. 13

DETAILED DESCRIPTION

Figure 1:
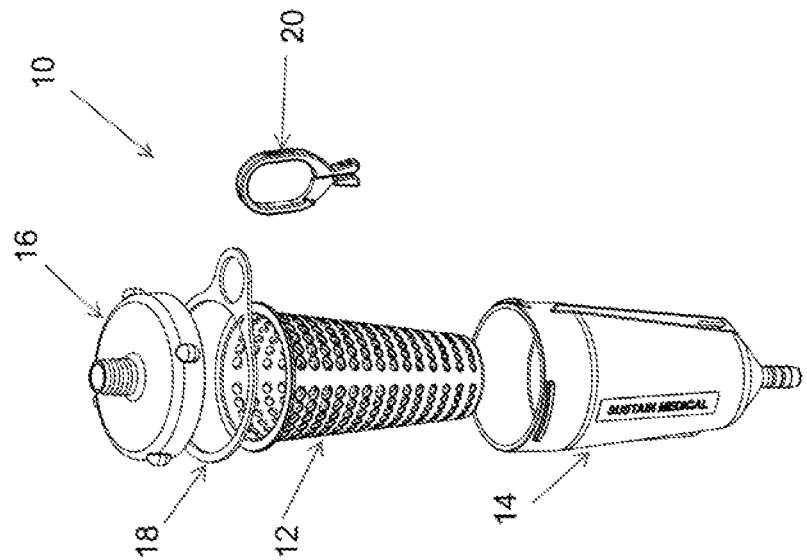
FIG. 1 is an exploded perspective view of a filter assembly according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 2:
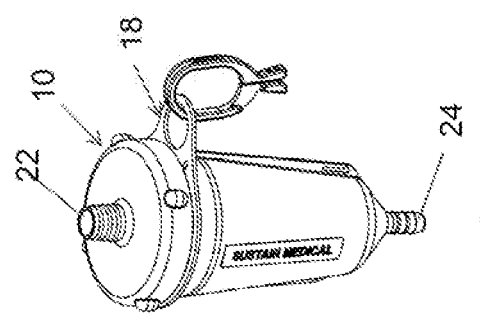
FIG. 2 is a perspective view of the assembled filter assembly shown in FIG. 1.
Figure 3:
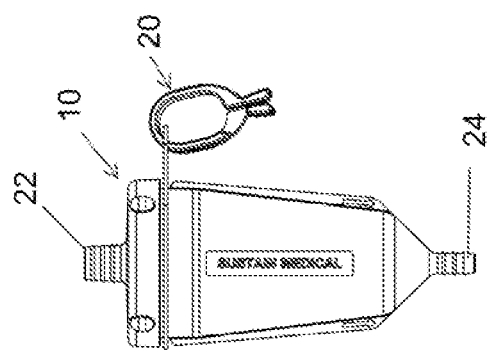
FIG. 3 is a side view of the assembled filter assembly shown in FIG. 2.
Figure 17:
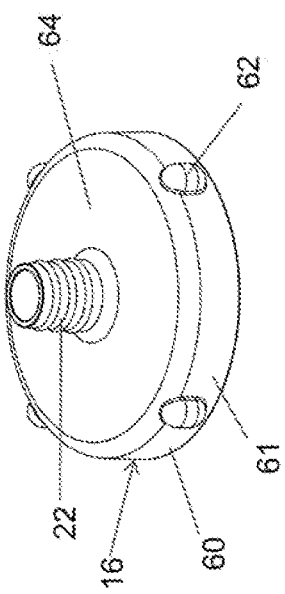
FIG. 17 is a perspective view of a cap of the filter assembly shown in FIG. 1
Figure 22:
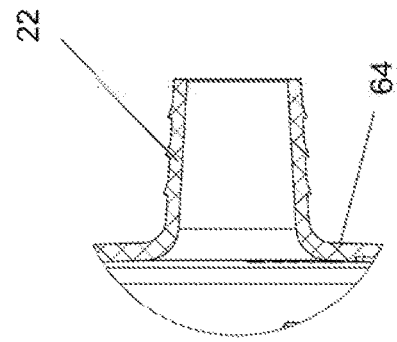
FIG. 22 is an enlarged cross-sectional view of the top of the cap shown in FIG. 21.
Figure 21:
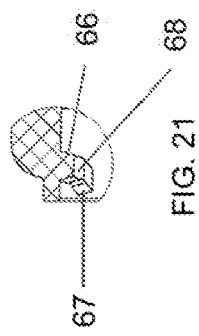
FIG. 21 is an enlarged cross-sectional view of the side of the cap shown in FIG. 20.
Figure 20:
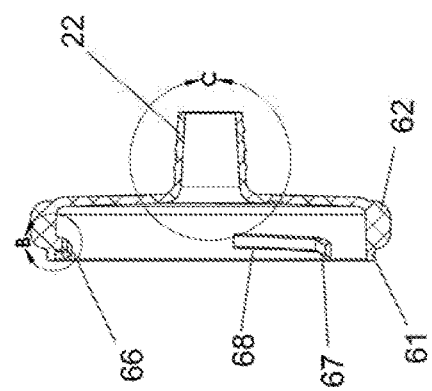
FIG. 20 is a side cross-sectional view of the cap shown in FIG. 19.
Figure 18:
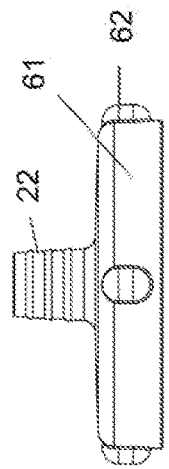
FIG. 18 is side view of the cap shown in FIG. 17.
Figure 19:
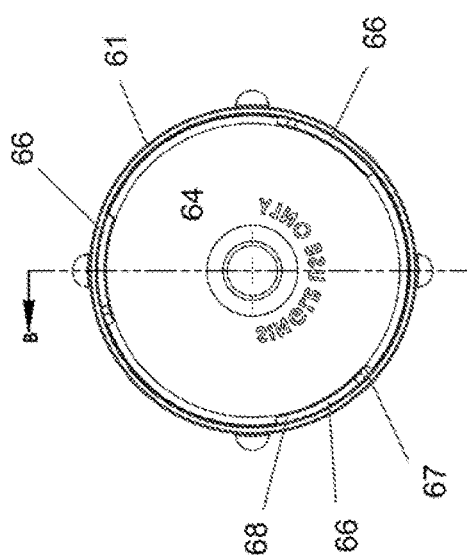
FIG. 19 is a top view of the cap shown in FIG. 17.

A filter assembly 10 includes a filter element 12, disposed within container 14 enclosed by a cap 16, as shown in FIGS. 1-3. A support ring 18 is captured between the cap and the container and is configured to receive a clip 20 used to support the filter assembly at the surgical site. The filter assembly includes an inlet tube fitting 22, incorporated into the cap 16, and an outlet tube fitting 24, incorporated into the container 14, with each fitting configured to engage standard medical tubing used in a surgical suction system. In particular, the inlet fitting 22 may be coupled to a tube engaged to a suction tool, such as a suction wand used at the surgical site to remove fluid and debris from a surgical wound. The outlet fitting 24 may be coupled to a tube that is connected to a suction source and/or fluid container for receive the fluids suctioned from the surgical site.

Details of the filter element 12 are shown in FIGS. 4-10. The filter element includes a one-piece body 30 that is configured to be readily formed by injection molding. In one embodiment, the body 30 is formed of a clear or substantially transparent medical grade thermoplastic elastomer, such as Medalist® MD-50273 low density thermoplastic elastomer, produced by Teknor Apex Company. The filter body includes a mouth 31 open to an interior chamber 32 defined by a tapered or conical cylindrical wall 35. A bottom wall 40 closes the bottom of the interior chamber 32 so that the filter body is a truncated conical body. In one specific embodiment, the tapered wall is conically tapered at a 12° angle from the mouth 31 to the bottom wall 40. The body 30 can have a length of about 100 mm and a mouth opening diameter of about 62 mm. The bottom wall 40 may be tapered at an angle of 4° relative to the horizontal.

The tapered wall 35 defines a plurality of orifice arrays, with three such arrays 37A, 37B, 37C identified in the figures. Each array includes a plurality of orifices, each having a uniform diameters, while the diameters of the orifices decrease with each successive array. Thus, in one specific embodiment, the orifices in the uppermost array 37A have a diameter of about 4.0 mm, whereas the orifices in the lowermost array 37C can have a diameter of about 2.0 mm. The orifice diameters decrease with each successive array from the uppermost array 37A to the lowermost array 37C. In one specific embodiment, each array includes four orifice sections separated by a support column 39 that extends along the length of the conical wall 35, as best shown in FIG. 5. In the specific embodiment, fourteen orifice arrays are provided along the length of the filter body 30. The orifices are sized to prevent passage of debris collected from the surgical site, such as bone pieces that are typical in an orthopaedic surgical procedure. The filter element 12 is sized to collect a significant amount of debris while still permitting relatively free flow of fluid through the filter assembly. The larger orifices in the uppermost portion of the filter element ensures sufficient suction and fluid flow even as debris is collected in the bottom of the filter element. The bottom wall 40 is also provided with a plurality of orifice arrays 41, as shown in FIG. 8. The diameter of the orifices in the bottom wall array 41 can be the same as the orifice diameters for the lowermost array 37C, such as 2.0 mm in the specific embodiment.

In one aspect of the present disclosure, the body 30 of the filter element 12 includes a circumferential flange 42 at the mouth 31 of the element. As explained below, the flange is used to mount the filter element within the container 14. In one specific embodiment, the flange 42 can have an annular width of about 2.5 mm and a thickness of about 1.75 mm.

As indicated above, the filter element 12 is configured to be injection molded. Hence, the plurality of orifices, such as the orifices in the arrays 37A, 37B and 37C, are formed with a draft angle relative to the outer surface of the conical wall 35. It can be appreciated that the wall thicknesses and filet radius between the conical wall and the flange are calibrated for a conventional injection molding process.

Details of the container 14 are shown in FIGS. 11-16. The container includes a container body 54 with a mouth 46 opening to an interior chamber 47. The body 45 includes an upper cylindrical wall 50 that extends to a conical cylindrical wall 51 that corresponds to the conical wall of the filter element 12. The interior 47 of the container is sized and configured to receive the filter element 12 therein with the annular flange 42 resting on the upper edge 52 of the circumferential wall 50. The conical cylindrical wall 51 of the container 14 is radially offset from the conical cylindrical wall 35 of the filter element when the filter element is supported within the interior 47 in order to provide a fluid flow path between the filter element and the container. In one specific embodiment, the two cylindrical walls are sized to provide a 0.5 mm radial gap between the walls. The container body 45 is configured to be injection molded of a plastic material. In one specific embodiment the body is formed of a clear or substantially transparent medical grade polycarbonate, such as CALIBRE™ MEGARAD™ 2081 2.5 MRAD polycarbonate produced by Trinseo S. A.

The container body 45 terminates in a conical bottom wall 56 from which the outlet tube fitting 24 extends. The body 45 includes a pair of diametrically opposed fins 45 that provide stiffness for the body. The fins may also incorporate arrows 54 indicating the direction of fluid flow through the filter assembly in order to ensure that the filter assembly is properly integrated into the suction flow path.

A plurality of thread segments 58 are defined in the upper cylindrical wall 50, as best seen in FIGS. 12-13. In one specific embodiment, three such thread segments are uniformly spaced around the circumference of the wall 50. As shown in FIG. 15, the thread segments are separated by 66° so that each thread segment subtends an angle of 56°. In one aspect of the present disclosure, the thread segments are configured as a triple lead thread (hence the three segments) with a pitch of 8.0 mm. The threads are configured to engage the cap 16, as described herein.

Details of the cap 16 are shown in FIGS. 17-22. The cap includes a body 60 that is configured for injection molding. Like the container body 45, the cap body 60 may also be formed of a clear or substantially transparent thermoplastic such as CALIBRE™ MEGARAD™ 2081 2.5 MRAD polycarbonate produced by Trinseo S. A. The body 60 includes a cylindrical wall 61 that is sized to fit over the mouth 46 and around the upper cylindrical wall 50 of the container body 45. Grip protrusions 62 may be formed on the wall 61 to facilitate manual gripping of the cap to thread the cap onto the container body. The cap includes a top wall 64 from which the inlet tube fitting 22 protrudes.

The cap body 60 further defines three internal thread segments 66 on the cylindrical wall 61. In one aspect, the thread segments 66 are configured to engage the thread segments 58 of the container 14. More particularly, the thread segments 58, 66 are configured so that the cap 16 can be tightened onto the mouth of the container 14 to clamp the annular flange 42 of the filter element 12 between the top wall 64 of the cap and the upper edge 52 of the container body. As with the thread segments 58, the thread segments 66 of the cap are symmetrically spaced around the circumference of the wall 61. The thread segments 66 each subtend an angle of about 41° so that the thread segments 66 can be initially positioned in the gap between the thread segments 58 of the container body. The cap can be rotated relative to the container so that the thread segments of the cap engage the thread segments of the container.

In one feature of the filter assembly disclosed herein, the thread segments 66 are dual-pitch triple lead threads. The thread segments thus include an initial lead-in pitch portion 67 and a subsequent trailing fine pitch portion 68. In one embodiment, the lead-in pitch is no more than ten times greater than the trailing pitch. In a specific embodiment, the lead-in pitch portion is configured to have a pitch of 80 mm, while the fine pitch portion is configured to have a thread pitch of 8.0 mm. The coarse pitch of the lead-in pitch portion 67 facilitates engagement of the thread segments between the cap and the container and provides an easy start to the threaded engagement. Once the cap is initially threadedly engaged to the container, the fine-pitch portion 68 engages the container thread segments to provide an increased clamping force on the annular flange 42 of the filter element. This configuration allows the annular flange to operate as a fluid-tight sealing gasket as the flange is slightly compressed between the cap wall 64 and the housing edge 52. The thread segments 58 of the container and the fine pitch portions 68 of the cap have lengths sufficient to clamp the filter element flange when the cap is fully tightened onto the container.

In the illustrated embodiment, three mating thread segments are employed. However, more than three segments are contemplated, with appropriate modifications to the thread pitch of the trailing portion. In it understood that with more than three thread segments, the trailing fine pitch portion 68 of the modified segments is necessarily shorter since the spacing between mating thread segments 58 must be smaller. In order to achieve the same fluid tight seal between the flange 42 and the container body as with the three thread segment embodiment, the four segment embodiment, for instance, requires a coarser pitch to drive the cap the same distance toward the flange as in the three segment embodiment. Thus, whereas the fine pitch portion 68 of the three segment embodiment can have a pitch of 80, the fine pitch portion for a four segment embodiment can have a pitch of 60. The lead-in pitch can be 8 as in the three segment embodiment.

Figure 23:
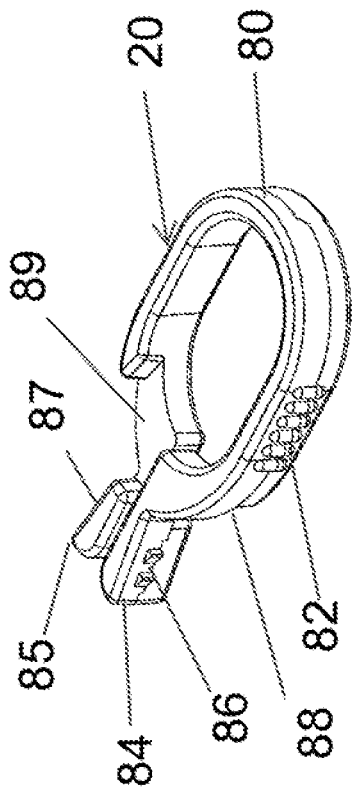
FIG. 23 is a perspective view of a support ring of the filter assembly shown in FIG. 1.

The filter assembly 10 can include the support ring 18, which is shown in detail in FIG. 23. The ring includes an annular body 70 defining an opening 71, in which the opening has a diameter sized to be received over the upper cylindrical wall 50 of the container body 45 but smaller than the effective diameter of the fins 53 so that the ring can be trapped between the cap 16 and the fins. The body defines a notch 72 intersecting the opening to facilitate slight deformation of the ring for placement onto the container body 45. The ring further includes a loop 74 projecting laterally from the annular body 72, in which the loop is configured to receive an attachment component, such as the clip 20.

Figure 26:
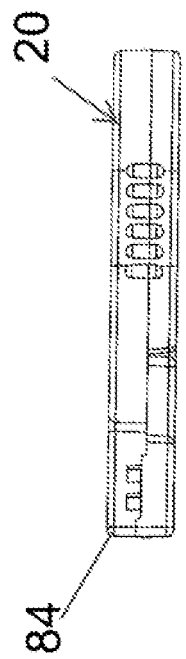
FIG. 26 is a side view of the clip shown in FIG. 24.
Figure 25:
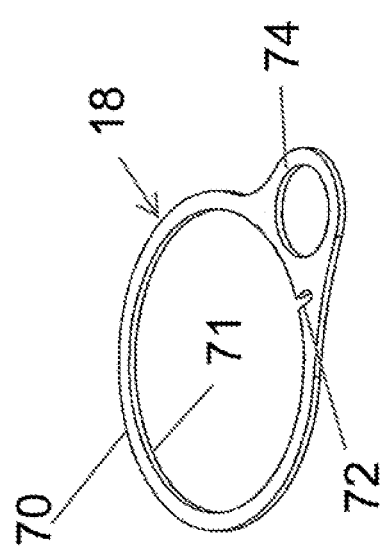
FIG. 25 is a top view of the clip shown in FIG. 24.
Figure 24:
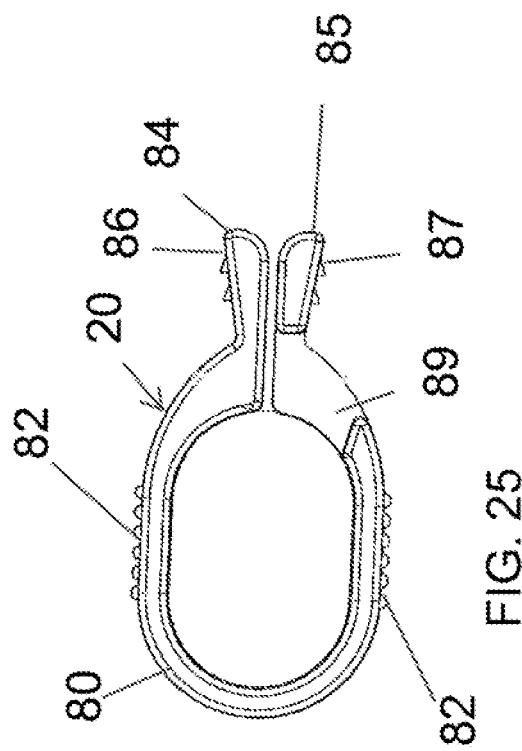
FIG. 24 is a perspective view of a clip of the filter assembly shown in FIG. 1.

As shown in FIGS. 24-26, the clip includes a one-piece somewhat elongated or oval-shaped body 80 with grip surfaces 82 on opposite sides of the body. The body is defines as an open ring with the adjacent ends 84, 85 defining mating latch elements with latch surfaces 86, 87, respectively, that can engage when the latch elements overlap. The annular body 70 defines indentations 88, 89 at the respective adjacent ends, configured to overlap each other to place the latch surfaces into contact. The clip 18 can thus be readily latch and unlatched as required.

The present disclosure should be considered as illustrative and not restrictive in character. It is understood that only certain embodiments have been presented and that all changes, modifications and further applications that come within the spirit of the disclosure are desired to be protected.

What is claimed is:

1. A filter assembly for use with a surgical suction tool for removing fluid and debris from a surgical site, the filter assembly comprising:
   a filter element having an elongated truncated conical body including a mouth at one end, a closed bottom at an opposite end and a conically tapered wall between the mouth and bottom to define an interior chamber, the tapered wall defining a plurality of orifice arrays spaced along the length of the conical body, each of the plurality of orifice arrays including a plurality of orifices through the wall, the plurality of orifices in each orifice array having a successively decreasing diameter with each successive orifice array along the length of the body, the filter element further including an annular flange at the mouth of the filter element;
   a container for receiving the filter element, the container including a cylindrical upper wall defining a mouth, a conically tapered wall integral with the cylindrical upper wall and a conical bottom wall integral with the conically tapered wall and terminating in an outlet tube fitting adapted to engage a surgical tube connected to a suction source and/or a fluid container, wherein the conically tapered wall is configured to coincide with a lower portion of the conically tapered wall of the filter element when the flange of the filter element is seated on the cylindrical upper wall at the mouth of said container, the conically tapered walls of the filter element and the container defining a radial space therebetween along the entire length of the filter element to permit fluid flow around the filter element and through the container to the outlet tube fitting;
   a cap sized and configured to cover the mouth of said container, said cap including a cylindrical wall sized to encircle an upper portion of the cylindrical upper wall of the container to close the mouth and a top wall defining an inlet tube fitting adapted to engage a surgical tube connected to a suction tool; and
   a threaded interface between the cylindrical wall of the cap and the upper cylindrical wall of the container, the threaded interface including a dual pitch multiple lead thread.

2. The filter assembly of claim 1, wherein the threaded interface includes:
   at least three thread segments defined on an exterior surface of said upper cylindrical wall of said container at a first pitch;
   at least three dual pitch segments defined on an interior surface of said cylindrical wall of
   said cap, each segment including an initial lead-in portion at said first pitch and a trailing portion defined at a second pitch less than said first pitch.

3. The filter assembly of claim 2, wherein the first pitch is no more than ten times greater than said second pitch.

4. The filter assembly of claim 3, wherein said first pitch is 80.0 mm and said second pitch is 8.0 mm.

5. The filter assembly of claim 2, wherein said trailing portion of each of said at least three dual pitch segments of said cap and said at least three thread segments of said upper cylindrical wall of said container having a length sufficient to clamp said flange of said filter element between said cylindrical upper wall of said container and said cap when said threaded interface is tightened.

6. The filter assembly of claim 1, wherein said conically tapered wall defines a plurality of support columns along the length of said filter element, said support columns circumferentially separating a number of the plurality of orifices within each of the plurality of orifice arrays, and said support columns being free of orifices.

7. The filter assembly of claim 6, comprising four support columns evenly spaced around the circumference of said conically tapered wall of the filter element.

8. The filter assembly of claim 1, wherein at least the filter element and the container are formed of a substantially transparent material.

9. The filter assembly of claim 1, wherein said bottom wall of said filter element defines a plurality of orifices therethrough.

* * * * *